US008309695B2

(12) United States Patent
Laurent et al.

(10) Patent No.: US 8,309,695 B2
(45) Date of Patent: Nov. 13, 2012

(54) MARKING REAGENTS BEARING DIAZO AND NITRO FUNCTIONS, METHODS FOR THE SYNTHESIS OF SUCH REAGENTS AND METHODS FOR DETECTING BIOLOGICAL MOLECULES

(75) Inventors: Alain Laurent, Grenoble (FR); Ali Laayoun, Colombe (FR); Mitsuharu Kotera, Strasbourg (FR)

(73) Assignees: Biomerieux, Marcy l'Etoile (FR); CNRS, Paris (FR); Universite de Strasbourg, Strasbourg (FR)

( * ) Notice: Subject to any disclaimer, the term of this patent is extended or adjusted under 35 U.S.C. 154(b) by 309 days.

(21) Appl. No.: 12/451,502

(22) PCT Filed: Jun. 9, 2008

(86) PCT No.: PCT/FR2008/051026
§ 371 (c)(1),
(2), (4) Date: Nov. 16, 2009

(87) PCT Pub. No.: WO2009/001017
PCT Pub. Date: Dec. 31, 2008

(65) Prior Publication Data
US 2010/0136538 A1 Jun. 3, 2010

(30) Foreign Application Priority Data
Jun. 11, 2007 (FR) .................................. 07 55639

(51) Int. Cl.
*C07C 245/14* (2006.01)
*C12Q 1/68* (2006.01)
(52) U.S. Cl. .......... 534/558; 534/560; 534/565; 436/56; 436/63; 436/501; 436/544; 436/546
(58) Field of Classification Search ........................ None
See application file for complete search history.

(56) References Cited

U.S. PATENT DOCUMENTS

| | | | |
|---|---|---|---|
| 4,507,466 A | 3/1985 | Tomalia et al. | |
| 4,568,737 A | 2/1986 | Tomalia et al. | |
| 4,672,040 A | 6/1987 | Josephson | |
| 4,683,195 A | 7/1987 | Mullis et al. | |
| 4,683,202 A | 7/1987 | Mullis | |
| 4,775,745 A | 10/1988 | Ford et al. | |
| 4,800,159 A | 1/1989 | Mullis et al. | |
| 5,234,809 A | 8/1993 | Boom et al. | |
| 5,328,824 A | 7/1994 | Ward et al. | |
| 5,399,491 A | 3/1995 | Kacian et al. | |
| 5,449,767 A | 9/1995 | Ward et al. | |
| 5,489,653 A | 2/1996 | Charles et al. | |
| 5,695,936 A | 12/1997 | Mandrand et al. | |
| 5,750,338 A | 5/1998 | Collins et al. | |
| 6,033,853 A | 3/2000 | Delair et al. | |
| 6,083,708 A | 7/2000 | Singh et al. | |
| 6,083,762 A | 7/2000 | Papen et al. | |
| 6,083,763 A | 7/2000 | Balch | |
| 6,110,426 A | 8/2000 | Shalon et al. | |
| 6,133,047 A | 10/2000 | Elaissari et al. | |
| 6,376,179 B1 | 4/2002 | Laayoun | |
| 6,489,114 B2 | 12/2002 | Laayoun et al. | |
| 6,521,341 B1 | 2/2003 | Elaissari et al. | |
| 6,537,783 B1 | 3/2003 | Guillou-Bonnici et al. | |
| 6,576,448 B2 | 6/2003 | Weissman et al. | |
| 6,632,662 B1 | 10/2003 | Broyer et al. | |
| 6,660,472 B1 | 12/2003 | Santoro et al. | |
| 6,686,195 B1 | 2/2004 | Colin et al. | |
| 6,818,398 B2 | 11/2004 | Bavykin et al. | |
| 6,875,858 B1 | 4/2005 | DeFrancq et al. | |
| 7,060,441 B2 * | 6/2006 | Bourget et al. | 435/6.12 |
| 7,338,805 B2 | 3/2008 | Bourget et al. | |
| 2002/0081586 A1 | 6/2002 | Laayoun et al. | |
| 2002/0155496 A1 | 10/2002 | Charles et al. | |
| 2004/0005614 A1 | 1/2004 | Kurn et al. | |
| 2004/0091451 A1 | 5/2004 | Charreyre et al. | |
| 2008/0032288 A1 | 2/2008 | Laayoun et al. | |
| 2008/0138908 A1 * | 6/2008 | Amano | 436/87 |
| 2009/0023140 A1 * | 1/2009 | Furuta et al. | 435/6 |

FOREIGN PATENT DOCUMENTS

| | | |
|---|---|---|
| DE | 39 10 151 A1 | 10/1990 |
| EP | 0 063 879 A2 | 11/1982 |
| EP | 0 097 373 A2 | 1/1984 |
| EP | 0 201 184 A2 | 12/1986 |
| EP | 0 286 898 A2 | 10/1988 |

(Continued)

OTHER PUBLICATIONS

Hawthorne, Susan J. et al., "The Synthesis and Utilization of 2,4-Dinitrophenyl-Labeled Irreversible Peptidyl Diazomethyl Ketone Inhibitors", Analytical Biochemistry, 261(2), 131-138, 1998.* "2 Methods for the Preparation of Alkane, Alkene, and Alkyne Diazo Compounds," pp. 34-48.
E. Bayer et al., "The Use of the Avidin-Biotin Complex as a Tool in Molecular Biology," Methods of Biochemical Analysis, vol. 26 (1980), pp. 1-45.

(Continued)

Primary Examiner — Fiona T Powers
(74) Attorney, Agent, or Firm — Oliff & Berridge, PLC

(57) ABSTRACT

The present invention relates to a labeling reagent of formula:

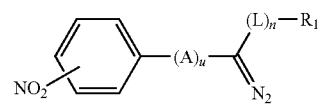

in which:
$R_1$ represents at least one detectable label,
L and A are each a linker arm,
n is an integer equal to 1, and
u is an integer between 0 and 2.
The present invention also describes a method of synthesizing said markers and also applications for the labeling of biological molecules, more particularly nucleic acids, with a labeling reagent bearing diazo and nitro functions. The invention is particularly suitable for use in the diagnostics field.

20 Claims, 6 Drawing Sheets

FOREIGN PATENT DOCUMENTS

| | | |
|---|---|---|
| EP | 0 302 175 A2 | 2/1989 |
| EP | 0 329 198 A2 | 8/1989 |
| EP | 0 350 407 B1 | 1/1990 |
| EP | 0 561 722 A1 | 9/1993 |
| EP | 0 567 841 A2 | 11/1993 |
| EP | 0 569 272 B1 | 11/1993 |
| EP | 0 669 991 B1 | 9/1995 |
| EP | 0 827 552 B1 | 3/1998 |
| FR | 2 607 507 A1 | 6/1988 |
| WO | WO 88/04289 A1 | 6/1988 |
| WO | WO 90/01069 A1 | 2/1990 |
| WO | WO 90/06995 A1 | 6/1990 |
| WO | WO 90/08838 A1 | 8/1990 |
| WO | WO 91/02818 A1 | 3/1991 |
| WO | WO 93/16094 A2 | 8/1993 |
| WO | WO 95/08000 A2 | 3/1995 |
| WO | WO 97/35031 A1 | 9/1997 |
| WO | WO 97/45202 A1 | 12/1997 |
| WO | WO 98/05766 A1 | 2/1998 |
| WO | WO 99/15621 A1 | 4/1999 |
| WO | WO 99/35500 A1 | 7/1999 |
| WO | WO 99/53304 A1 | 10/1999 |
| WO | WO 99/65926 A1 | 12/1999 |
| WO | WO 00/05338 A1 | 2/2000 |
| WO | WO 00/07982 A1 | 2/2000 |
| WO | WO 00/40590 A2 | 7/2000 |
| WO | WO 00/60049 A1 | 10/2000 |
| WO | WO 01/44506 A1 | 6/2001 |
| WO | WO 01/92361 A1 | 12/2001 |
| WO | WO 02/090319 A1 | 11/2002 |
| WO | WO 02/090584 A2 | 11/2002 |
| WO | WO 2005/092910 A1 | 10/2005 |

OTHER PUBLICATIONS

S. Agrawal, "Protocols for Oligonucleotides and Analogs, Synthesis and Properties," Methods in Molecular Biology, vol. 20, pp. 487-496, Humana Press, New Jersey.

B. Charleux et al., "Radical-initiated Copolymers of Styrene and p-Formylstyrene, 1 Solution Copolymerization and Characterization," Makromol. Chem., vol. 193 (1992), pp. 187-203.

J. Cheng et al., "Microchip-based Devices for Molecular Diagnosis of Genetic Diseases," Molecular Diagnosis, vol. 1, No. 3 (1996), pp. 183-200.

J. Cheng et al., "Preparation and Hybridization Analysis of DNA/RNA from *E. coli* on Microfabricated Bioelectronic Chips," Nature Biotechnology, vol. 16 (1998), pp. 541-546.

X. Creary, "Tosylhydrazone Salt Pyrolyses: Phenyldiazomethanes," Organic Synthesis, Coll., vol. 7 (1990), pp. 438-443.

M. Egholm et al., "Peptide Nucleic Acids (PNA) Oligonucleotide Analogues with an Achiral Peptide Backbone," J. Am. Chem. Soc., vol. 114 (1992), pp. 1895-1897.

F. Ginot, "Oligonucletide Micro-Arrays for Identification of Unknown Mutations: How Far from Reality?," Human Mutation, vol. 10 (1997), pp. 1-10.

T.W. Greene et al., "Protective Groups in Organic Synthesis," 3$^{rd}$ Edition, John Wiley and Sons, Inc., New York (1991), pp. 230-245.

T. L. Holton et al., "Advantageous Syntheses of Diazo Compounds by Oxidation of Hydrazones with Lead Tetraacetate in Basic Environments," J. Org. Chem. (1995), vol. 60, pp. 4725-4729.

S. Hunt, "The Non-Protein Amino Acids," Chemistry and Biochemistry of the Amino Acids, edited by G.C. Barett, Chapman and Hall, London (1985), pp. 55-138.

W. Jencks et al., "Reactivity of Nucleophilic Reagents toward Esters," J. Amer. Chem Soc., vol. 82 (1960), pp. 1778-1786.

A. Laayoun et al., "Aryldiazomethanes for Universal Labeling of Nucleic Acids and Analysis on DNA Chips," Bioconjugate Chem. (2003), vol. 14, pp. 1298-1306.

P. Langer et al., "Enzymatic Synthesis of Biotin-labeled Polynucleotides: Novel Nucleic Acid Affinity Probes," Proc. Natl. Acad. Sci. USA, vol. 78, No. 11 (1981), pp. 6633-6637.

T. Livache et al., "Preparation of a DNA Matrix Via an Electrochemically Directed Copolymerization of Pyrrole and Oligonucleotides Bearing a Pyrrole Group," Nucleic Acids Research (1994), vol. 22, No. 15, 2915-2921.

G. M. Makrigiorgos et al., "Fluorescent Labeling of Abasic Sites: A Novel Methodology to Detect Closely-Spaced Damage Sites in DNA," Int. J. Radiat. Biol. (1998), vol. 74, No. 1, pp. 99-109.

M. O'Donnell et al., "Reporter Groups for the Analysis of Nucleic Acid Structure," Bioorganic Chemistry: Nucleic Acids, Oxford University Press (1996), pp. 216-243.

M. Oivanen et al., "Kinetics and Mechanisms for the Cleavage and Isomerization of the Phosphodiester Bonds of RNA by Bronsted Acids and Bases," Chem. Rev., vol. 98 (1998), pp. 961-990.

T. Okamoto et al., "Microarray Fabrication with Covalent Attachment of DNA Using Bubble Jet Technology," Nature Biotechnology, vol. 18 (2000), pp. 438-441.

G. Pratviel et al., "DNA and RNA Cleavage by Metal Complexes," Adv. Org. Chem., vol. 45 (1998), pp. 251-312.

G. Pratviel et al., "Carbon-Hydrogen Bonds of DNA Sugar Units as Targets for Chemical Nucleases and Drugs," Angew. Chem. Int. Ed. Engl., vol. 34 (1995), pp. 746-769.

G. Ramsay, "DNA Chips: State-of-the Art," Nature Biotechnology, vol. 16 (1998), pp. 40-44.

J. Randolph et al., "Stability, Specificity and Fluorescence Brightness of Multiply-labeled Fluorescent DNA Probes," Nucleic Acids Research (1997), vol. 25, No. 14, pp. 2923-2929.

M. Shiga et al., "Synthesis of a Novel Biotin Derivative That Bears a Diazo Group as the Reactive Site," Analytical Sciences.(1993), vol. 9, pp. 553-556.

M. Shiga et al., "Fluorescence Detection of DNA Using a Novel Peroxidase Substrate, 4-(4-Hydroxyphenylcarhamoyl)butanoic. Acid," Analytical Sciences (1995), vol. 11, pp. 591-595.

D. Sigman et al., "Chemical Nucleases," Chem. Rev., vol. 93 (1993), pp. 2295-2316.

W. C. Still et al., "Rapid Chromatographic Technique for Preparative Separations with Moderate Resolution," J. Org. Chem. (1978), vol. 43, No. 14, pp. 2923-2925.

S. Wong, "Chemistry of Protein Conjugation and Cross-Linking," CRC Press (1991) pp. 16-45.

A. Troesch et al., "Mycobacterium Species Identification and Rifampin Resistance Testing with High-Density DNA Probe Arrays," Journal of Clinical Microbiology (Jan. 1990), vol. 37, No. 1, pp. 49-55.

Jul. 25, 2002 International Search Report issued in International Application No. PCT/FR02/01543.

Aug. 9, 2005 International Search Report issued in International Application No. PCT/FR2005/050192.

Jan. 14, 2009 International Search Report issued in International Application No. PCT/FR2008/051026.

Jul. 30, 2004 Office Action issued in U.S. Appl. No. 10/137,454, now U.S. Patent No. 7,338,805 B2.

Feb. 23, 2005 Office Action issued in U.S. Appl. No. 10/137,454, now U.S. Patent No. 7,338,805 B2.

Jul. 11, 2005 Office Action issued in U.S. Appl. No. 10/137,454, now U.S. Patent No. 7,338,805 B2.

Feb. 6, 2006 Office Action issued in U.S. Appl. No. 10/137,454, now U.S. Patent No. 7,338,805 B2.

Mar. 29, 2007 Office Action issued in U.S. Appl. No. 10/137,454, now U.S. Patent No. 7,338,805 B2.

Mar. 18, 2005 Office Action issued in U.S. Appl. No. 10/137,460, now U.S. Patent No. 7,060,441 B2.

Jan. 7, 2009 Office Action issued in U.S. Appl. No. 10/590,973.

Jul. 22, 2009 Office Action issued in U.S. Appl. No. 10/590,973.

Oct. 12, 2009 International Search Report issued in International Application No. PCT/FR2009/051511.

U.S. Appl. No. 13/001,712, filed Dec. 28, 2010, Alain Laurent et al.

* cited by examiner

*meta* Nitro DCB (molecule 10)

*para* Nitro DCB (molecule 20)

BBP

MARKING REAGENTS BEARING DIAZO AND NITRO FUNCTIONS, METHODS FOR THE SYNTHESIS OF SUCH REAGENTS AND METHODS FOR DETECTING BIOLOGICAL MOLECULES

The present invention relates to new reagents for labeling biological molecules, to a method of synthesizing said labels, and to applications for the labeling of biological molecules more particularly in the field of diagnosis using nucleic acid analysis.

The prior art shows that there are numerous techniques for labeling nucleotides, oligonucleotides or nucleic acids.

A first technique involves attaching the label to the base, the base being either natural or modified. A second technique proposes binding the label to the sugar, which again may be natural or modified. A third method entails binding the label to the phosphate.

Labeling on the base has been used in particular in the approach involving labeling nucleic acids by incorporation of directly labeled nucleotides.

Labeling on the sugar is often used in the case of nucleic acid probes prepared by chemical synthesis.

Labeling on the phosphate has also been used to introduce functionalized arms and labels during the chemical synthesis of oligonucleotides.

In actual fact a skilled person who is required to perform labeling of a nucleotide, a nucleotide analogue or a nucleic acid is inclined to perform this binding to the base or to the sugar, which offer him or her greater convenience and a greater number of alternatives. This is what emerges, moreover, from a study of numerous documents, such as EP-A-0 329 198, EP-A-0 302 175, EP-A-0 097 373, EP-A-0 063 879, U.S. Pat. Nos. 5,449,767, 5,328,824, WO-A-93/16094, DE-A-3 910 151, EP-A-0 567 841, for the base, or EP-A-0 286 898, for the sugar.

Binding the label to the phosphate is a more complex technique than the technique which involves functionalizing the base or the sugar, and has been used to much less of an extent, particularly on account of the low reactivity of the phosphate (see, for example, Jencks W. P. et al., J. Amer. Chem. Soc., 82, 1778-1785, 1960). Similarly, in the review by O'Donnel and McLaughlin (Reporter groups for the analysis of nucleic acid structure, pp. 216-243 in "Bioorganic Chemistry: Nucleic Acids", Ed Hecht S. M., Oxford University Press, 1996), relating to methods of introducing probes into oligonucleotide fragments, the effective alkylation of the internucleotide phosphodiester is considered to be impossible.

Patent application WO-A-99/65926 describes a method of labeling a synthetic or natural ribonucleic acid (RNA) which comprises fragmenting the RNA and carrying out labeling at the terminal phosphate. This document describes a certain number of functions which can be used for the labeling in connection with the fragmentation, such as the functions hydroxyl, amine, hydrazine, alkoxyamine, alkyl halide, and benzyl-type alkyl halide, and more particularly the 5-(bromomethyl)fluorescein derivative. These functions allow nucleic acids to be labeled, but must be combined with a fragmentation step in order to obtain effective labeling, since this labeling takes place on the phosphate liberated during the fragmentation. Furthermore, it is necessary to add a large excess of labeling reagent relative to the RNA in order to obtain effective labeling, and this gives rise to background noise problems generated by the excess label. Lastly, this method does not operate effectively on double-stranded DNA.

There is therefore a need for new reagents which are effective in terms of labeling yield, which are specific in terms of the labeling position, and, more particularly, which do not adversely affect the properties of hybridization of the bases involved in the formation of the double helix, via hydrogen bonds, which can be used both for DNA and RNA, and, finally, which allow labeling equally of nucleotides, of oligonucleotides, and of nucleic acids, whether they be natural or prepared by transcription, by reverse transcription or by enzymatic amplification.

The Applicant has already provided new labels of this kind which meet the above-stated conditions and which utilize the diazomethyl function as a reactive function for labeling. This is the case, for example, in patent applications WO-A-02/090319, WO-A-02/090584, and WO-A-2005/092910.

Thus the diazomethyl function (of formula —$C(N_2)$—) has already been used for the alkylation of phosphate groups, but a certain number of problems arise. First, reagents which incorporate at least one diazo function are generally unstable by themselves, which poses problems for the use of these reagents in a labeling kit; this is totally unacceptable if a function of the labeled product is to demonstrate the presence of a biological target molecule in any sample.

Finally, reagents bearing the diazomethyl function and in association with certain labels, such as biotin, have a low solubility in water, which leads to the use of organic solvents miscible in water for coupling with biological molecules which are soluble only in water or in aqueous buffers. However, these solvents, if used at too high a concentration in the labeling reaction, risk triggering the precipitation of the biomolecules. There is therefore a need for labeling reagents which are sufficiently soluble in aqueous media.

The labeling reagents recommended by documents WO-A-02/090319, WO-A-02/090584 (first-generation molecules), and WO-A-2005/092910 (second-generation molecules) as mentioned above also solve these technical problems. The reader is invited to refer to these documents for any further explanation which might through inadvertent omission be not included in the text setting out the present invention.

The present invention is a rational improvement to the existing molecules. This is because the first- and second-generation molecules have the drawback of being chemically unstable despite the improvement already made in this respect over that which existed before. Hence the labeling remains highly effective, since the results obtained are very good even over more than a year. In addition, their synthesis remains relatively complex. The third-generation molecules are much more stable and easier to synthesize, which has considerable advantages in terms of the expiry dates of kits containing these molecules, and of industrialization of the syntheses.

The first- and second-generation molecules are functionally stable over a year if they are kept at low temperature in an anhydrous organic solvent. The third-generation molecules are much more stable, functionally and chemically, in either liquid or dry medium. They can therefore be handled in an aqueous medium after having been kept in a dry state, by drying or lyophilization, for example, over a much longer period (between 10 and 100 times greater), which is not the case with the first-generation or second-generation molecules, which do not withstand lyophilization.

This industrial utilization of the third-generation molecules is particularly important in integrated devices or microsystems, where the chemistry involved must be highly efficient and robust, without casting doubt on the stability of certain reagents in the event of a problem.

However, although these molecules and labeling methods are particularly effective, the Applicant has succeeded in finding new molecules and new methods which further improve the efficiency of the labeling. The present invention provides a solution to respond to the problem of the stability of the first- and second-generation molecules. Thus, two new molecular functionalities have been combined in order to create new reagents. They are defined as follows:

the diazomethyl function possesses an aromatic group in alpha position, which is substituted one or more times by a nitro group ($NO_2$) in meta, para or ortho position.

in its alpha' position the diazo function possesses the group which allows detection. This group may be biotin or any other group which allows detection.

This second point is an entirely original feature relative to the first- and second-generation molecules, since previously the group which allows detection was still bonded to the aromatic moiety, the alpha' position being occupied at most only by at least one nonfunctional substituent.

It is notable that, although the ortho position of the diazo function relative to the nitro group, which are both borne by the ring, enhances the stability performance characteristics of the molecules according to the invention, the meta and para positions result in diazo compounds which are more stable, and are the substitution positions which are used preferentially. However, it is entirely possible further to improve the stability of the molecules whose diazo function is positioned ortho to the nitro group, by adding stabilization means, the problem being then that the synthesis is more complex.

The definitions of "multimeric structure", "detectable label", "indirect systems", "fluorophores" and other labels of interest, "conjugation", "biological molecule", "nucleic acid", "enzymatic amplification technique", "substantially aqueous solution", "homogeneous solution", "solid support", and "purification step" are given in patent application WO-A-2005/092910, to which the reader is invited to refer if need be.

Likewise the techniques of:
the grafting chemistry and
the introduction of phosphate at the 3' or 5' end of the nucleic acids,
are also described in this above patent application, and the reader is able in said document to find any information needed for full comprehension of the present invention.

Furthermore, the diazomethyl function borne by these third-generation molecules, following the example of the first- and second-generation molecules, allows covalent grafting of the nucleic acids on the support. The grafting is simple and the bonding is stable, relative to adsorption in particular, and permits coupling of the nucleic acid on the solid support, thereby further facilitating the subsequent hybridization steps by lessening the steric hindrance.

This new class of molecules is called Diazo Ketone Biotin (DKB) and is represented by the relatively temperature-stable labeling reagent of formula (A) below:

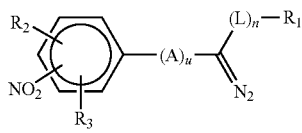

This third-generation DKB molecule comprises a spacer arm L, called a linker, and a label $R_1$, which may be composed of a detectable group, such as biotin, a hapten, a fluorophore, a fluorescent group, a luminescent group, etc.

L is a linker arm comprising a linear chain of at least two covalent bonds, and n is an integer equal to 1. Advantageously, and irrespective of the embodiment or variant set out before for the reactant, L comprises a unit —($O$—$CH_2$—$CH_2$)—, repeated from 1 to 20 times, preferably from 1 to 10 times, and more preferably from 2 to 5 times.

A is a linker arm comprising at least one covalent double bond allowing the conjugation of the diazo function with the aromatic ring, and u is an integer between 0 and 2, preferably 0 or 1.

In one particular embodiment, A is a linker arm comprising at least one ethylenic double bond which allows the diazomethyl function to be conjugated with the aromatic ring. The function of the linker arm A is to distance the diazomethyl function from the ring, in order to lessen the steric hindrance while retaining the stability of the diazomethyl function. By "conjugation" is meant the electronic delocalization of the aromatic ring along the carbon chain of the linker arm A. As an example, the arm A may have the following structure:

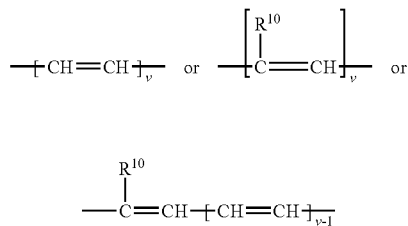

in which:

v is an integer between 1 and 10, and preferably v is 1 or 2, and $R^{10}$ is H or an alkyl group, and preferably $R^{10}$ is H, methyl or ethyl.

The radicals $R_3$ and $R_4$ represent, independently of one another: H, $NO_2$, Cl, Br, F, I, $R^2$-(L)$_n$-Y—X—, OR, SR, $NR_2$, R, NHCOR, CONHR or COOR, with R being alkyl or aryl.

According to a second embodiment, the labeling reagent is of formula (C) as described below:

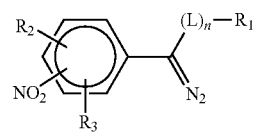

in which:

$R_1$ represents a detectable label or at least two detectable labels linked to one another by at least one multimeric structure, $R_3$ and $R_4$ represent, independently of one another: H, $NO_2$, Cl, Br, F, I, $R^2$-(L)$_n$-Y—X—, OR, SR, $NR^2$, R, NHCOR, CONHR or COOR, with R being alkyl or aryl, L is a linker arm comprising a linear chain of at least two covalent bonds, and n is an integer equal to 1.

According to a third embodiment, the labeling reagent is of formula (E), as described below:

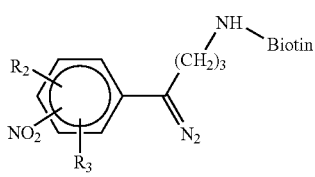

In whatever embodiment, the reagent is characterized in particular in that the nitro group is in meta or para position.

In one advantageous embodiment, the group $R_1$ is composed of a D-biotin residue of formula (F):

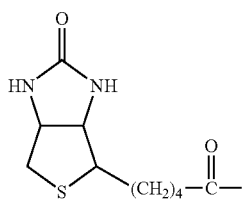

The invention likewise relates to a method of synthesizing a labeling reagent as described above, said method comprising the following steps:
a) a carboxylic acid derivative is reacted with the enolate of a lactone (Claisen reaction) to form a cyclic precursor,
b) said cyclic precursor is subsequently opened with a halogen acid to form a halogenated aromatic ketone,
c) the carbonyl function of the halogenated aromatic ketone is protected by a protective group to form a protected precursor,
d) said protected precursor is subjected to an amination reaction (Gabriel reaction) to form an aminated precursor,
e) said aminated precursor is deprotected to liberate the amine function, said amine function being reacted with a detectable label whose carboxyl function is activated to form a precursor comprising a detectable label,
f) the labeled precursor is subjected to a reaction for deprotection of the carbonyl function, to form a labeled and carbonylated precursor, and lastly
g) the labeled and carbonylated precursor is converted into a labeling reagent as described above by conversion of the carbonyl function into a diazo function (Bamford Stevens reaction).

In one embodiment, the method for labeling a biological molecule, more particularly a nucleic acid, comprises contacting a biological molecule, in homogeneous solution in a substantially aqueous buffer, with a reagent as described above.

The invention likewise relates to a labeled biological molecule obtainable by the method described above.

The invention also relates to a method of labeling and fragmenting a single-stranded or double-stranded nucleic acid, comprising the following steps:
fragmenting the nucleic acid;
attaching a label to at least one of the fragments via a labeling reagent selected from the reagents as described above,
said reagent coupling covalently and predominantly to at least one phosphate of said fragment.

In one embodiment, the method is characterized in that fragmenting and labeling are performed in two steps.

In another embodiment, the method is characterized in that fragmenting and labeling are performed in one step.

In whatever embodiment, the method is characterized in that labeling is performed in substantially aqueous homogeneous solution.

In whatever embodiment, the method is characterized in that fragmenting is performed enzymatically, physically or chemically.

The invention likewise relates to a labeled nucleic acid obtainable by the method, according to any of the embodiments described above.

The invention further relates to a kit for detecting a target nucleic acid, comprising a labeled nucleic acid such as that set out above.

The invention also relates to a solid support on which is bound a reagent as described above.

The invention also relates to a method of capturing nucleic acids, comprising the following steps:
providing a solid support on which is bound, directly or indirectly, at least one biological molecule or a nucleic acid, the biological molecule or the nucleic acid comprising a diazomethyl function,
contacting said support with a biological sample which may contain free nucleic acids, and
washing the solid support where the molecule or molecules is/are bound covalently at least to a nucleic acid.

The examples and figures attached represent particular embodiments and may not be considered as limiting the scope of the present invention.

Figure 1:
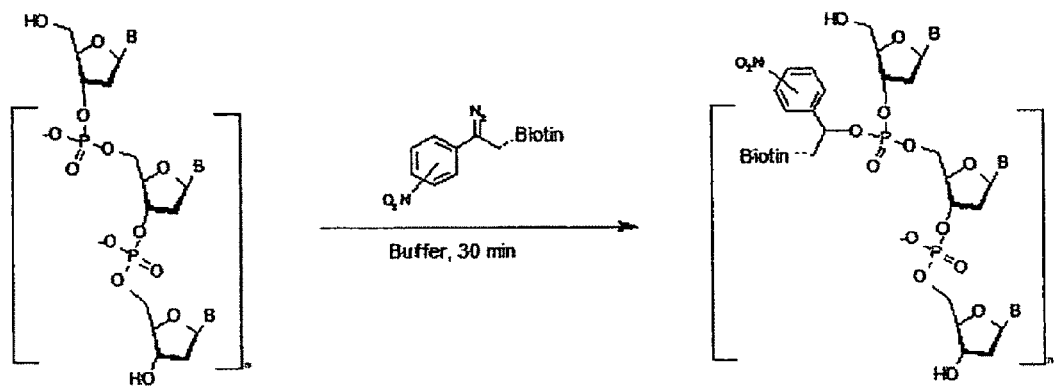
FIG. 1 shows a reaction scheme illustrating the labeling of a single-stranded nucleic acid, in either RNA or DNA form, by a molecule according to the invention.

In the examples described below, the following abbreviations will be used:
Ar: aromatic,
s: singlet,
d: doublet,
t: triplet,
qu: quintuplet, m: unresolved complex,
M: multiplet,
HPLC: high-pressure liquid chromatography,
TLC: thin-layer chromatography,
NMR: nucleomagnetic resonance,
Rf or TR: retention time,
DMSO-d6: deuterated dimethyl sulfoxide,
DMCF: dimethylcyclohexylammonium formate,
$CDCl_3$: deuterated chloroform, and
DMF: dimethylformamide
DCM: dichloromethane
MeOH: methanol
ACN: acetonitrile
MilliQ water: Millipore ultrapure water
DMAC: dimethylaminocinnamaldehyde.

General Conditions for the Synthesis and Analysis of the DKB Compounds:

These conditions are applicable to examples 1, 2, 3, and 4 below.

HPLC conditions (Waters Alliance 2795 HPLC system, diode array detector PDA 996, Empower software, version 2, and Waters XTerra MS C18 4.6×30 2.5 µm):

1°) Basic Method:
Eluent A: MilliQ water
Eluent B: ACN
Eluent C: 500 mM aqueous ammonia, pH 12
This corresponds to a linear gradient from 1% to 64% of acetonitrile (constant 5 mM of aqueous ammonia at pH=9) in 20 minutes.

2°) DMCF (Dimethylcyclohexylammonium Formate) Method:
Eluent A: MilliQ water
Eluent B: ACN
Eluent C: 500 mM DMCF, pH 7
This corresponds to a linear gradient from 1% to 64% of acetonitrile containing 5 mM DMCF at pH=7 in 20 minutes.

The 500 mmol/l solution of DMCF is prepared from 37 ml of dimethylcyclohexylamine, 9.4 ml of pure formic acid, and 200 ml of water. The pH is adjusted to 7 and the solution is made up to 500 ml with water.

3°) General Synthesis Conditions:

The thin-layer chromatographic analyses were carried out on Alugram® Macherey-Nagel SIL G/$UV_{254}$ 4×8 cm silica plates with UV detection at 254 nm, or with DMAC for the biotinylated products.

The products were purified by silica gel chromatography on Fluka Silica gel 60 (40-63 µm). The conditions for separation by flash chromatography (driven under argon) observe strictly the conditions described by Clark Still et al. (Clark Still, W.; Kahn, M.; Mitra, A. *J. Org. Chem.* 1978, 43, 2923-2925), namely a fixed height of 15 cm of silica, driven at a rate of 5 cm/min, the diameter of the column being dependent on the amount and Rf of the products to be purified.

The NMR spectra were recorded on a Brüker 200 MHz spectrometer. The chemical shifts (δ) are given in ppm relative to the peak of the solvent employed as internal standard ($CDCl_3$: 7.24 ppm; DMSO-d6: 2.49 ppm; $D_2O$: 4.80 ppm at 25° C.). The spectra are described using the following abbreviations: s=singlet, d=doublet, t=triplet, q=quadruplet, qu=quintuplet, m=unresolved complex, M=multiplet.

The mass spectra (MS) were obtained with an LCQ-ion trap instrument (Thermofinnigan, San Jose, Calif., USA) by electrospray ionization methods in positive mode, by infusion through a silica tube at 2 to 10 µl/min. The principal solvents used are DCM and MeOH.

EXAMPLE 1

Synthesis of Meta Nitro DKB

Objective:
To demonstrate the feasibility of the synthesis of a DKB molecule: meta Nitro DKB.

Figure 2:
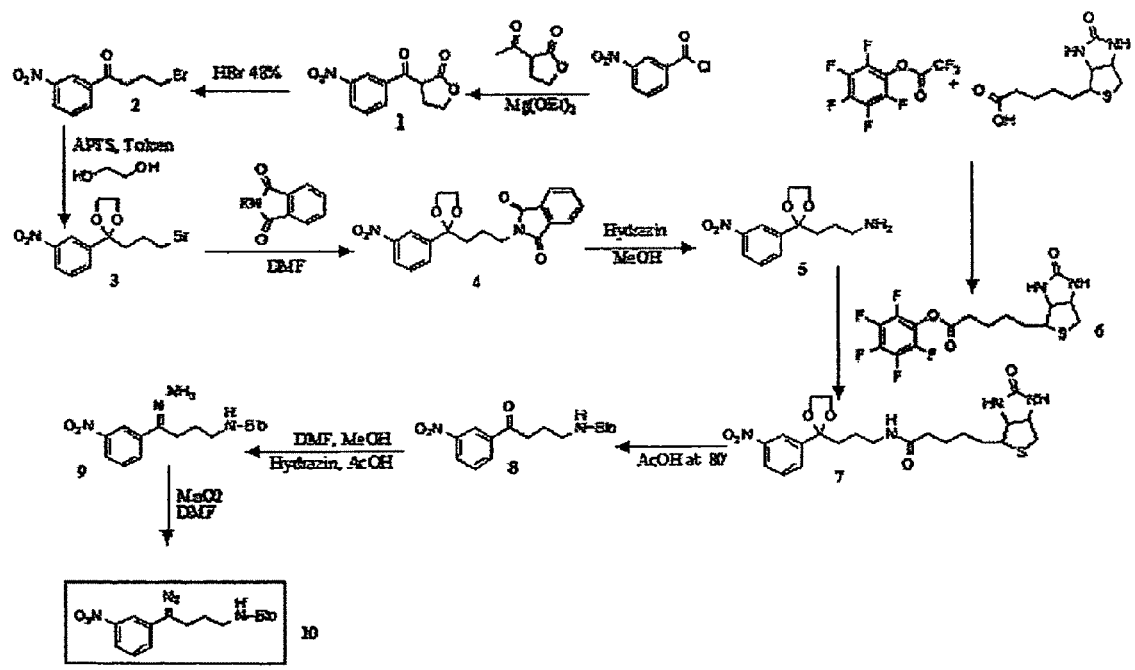
FIG. 2 represents a reaction scheme of the method of synthesizing a meta Nitro DKB molecule.

Procedure:
The synthesis proper is shown in FIG. 2. It begins with a molecule of meta Nitro benzyl chloride (3-nitrobenzoyl chloride), which is available commercially (Aldrich, Saint Quentin Fallavier, France).

Molecule 1
Magnesium ethoxide (5.41 g; 0.0473 mol) is suspended in chlorobenzene (33 ml), followed by α-acetyl-γ-butyrolactone (5.29 ml; 0.0492 mol), and the suspension is placed under argon and stirred and heated at 75° C. for 3 hours. After the reaction mixture has been cooled to ambient temperature and 3-nitrobenzoyl chloride (10 g; 0.0539 mol) in solution in chlorobenzene (16.4 ml) has been added, the system is heated at 40° C. for 2 hours.

The mixture is cooled to 10° C. before being hydrolyzed with 25 ml of 1 M sulfuric acid; the system is decanted and the organic phase (upper phase) is recovered, and is washed with 5% sodium hydrogencarbonate solution. The organic phase is then evaporated to dryness under reduced pressure before finally being purified on a silica gel column with a diameter of 7 cm and a height of 10.5 cm, with an elution rate of 5 cm/min. In a first phase, the eluent passed through the column is a 70/30 mixture of cyclohexane/ethyl acetate, followed by a 50/50 mixture. The fractions containing the expected product are combined and evaporated to dryness to give product 1 (8.17 g; yield=73.5%), which is employed directly in the following reaction.

TLC eluent: dichloromethane/methanol: 95/5
HPLC: DMCF method; TR=7.7 min

Molecule 2
Molecule 1 (5.50 g; 0.0234 mol) is suspended in a 48% strength aqueous solution of hydrobromic acid (33 ml; 6 v) which is refluxed for 2 hours. After the solution has been cooled to ambient temperature, the aqueous phase is extracted with 3 times 30 ml of dichloromethane. The organic phase is counterextracted with 5% sodium hydrogencarbonate and then dried over sodium sulfate, filtered and evaporated. This gives product 2 (6.06 g; yield=95.8%).

TLC eluent: dichloromethane/methanol: 95/5
HPLC: DMCF or basic method; TR=13.6 min
$^1H$ NMR (200 MHz, DMSO): 2.416 ppm (qu, 2H, C$\underline{H}_2$—$CH_2Br$), 3.426 ppm (t, 2H, $CH_2Br$), 3.279 ppm (t, 2H, C$\underline{H}_2$—CO), 7.738 ppm (t, 1H, Ar), 8.328 (d, 1H, Ar), 8.457 (d, 1H, Ar), 8.837 (s, 1H, Ar).

Molecule 3
In a round-bottom flask surmounted by a Dean Stark apparatus, compound 2 (4.00 g; 14.7 mmol), ethylene glycol (2.87 ml; 51.4 mmol), para-toluenesulfonic acid (139.6 mg; 7.35 mmol), and toluene (50 ml; 12.5 v) are mixed and then the mixture is refluxed for a total of 7 hours (5.5 hours at a set temperature of 130° C., then 1.5 hours at 150° C.). The reaction is complete, and the toluene is evaporated off under reduced pressure, the residue is taken up in 70 ml of ethyl acetate and washed with two times 50 ml of 250 mmol/l sodium hydrogencarbonate solution and then with two times 50 ml of water, the organic phase is dried over sodium sulfate, filtered and evaporated to dryness, before being purified by chromatography on silica gel (Φ=7 cm, h=7 cm, f=5 cm/min)

with as eluent the following: cyclohexane/ethyl acetate: 85/15. After this column, compound 3 is obtained (3.70 g; yield=79.6%).

TLC eluent: cyclohexane/ethyl acetate: 85/15
HPLC: basic method; TR=15.3 min
$^1$H NMR (200 MHz, DMSO): 1.90-2.10 ppm (m, 4H, C$\underline{H}_2$—CH$_2$—CH$_2$Br), 3.425 ppm (t, 2H, CH$_2$Br), 3.798 ppm (t, 2H, C$\underline{H}_2$—O), 4.081 ppm (t, 2H, CH$_2$—$\underline{O}$), 7.561 ppm (t, 1H, Ar), 7.75-7.85 ppm (m, 1H, Ar), 8.10-8.25 (m, 1H, Ar), 8.30-8.35 (m, 1H, Ar)

Molecule 4

Product 3 (3.70 g; 11.7 mmol) is dissolved in DMF (40 ml, 0.3 M), and then potassium phthalimide (3.25 g; 17.5 mmol) is added all at once and the mixture is heated at 155° C. for 15 minutes. The DMF is evaporated under reduced pressure and then the evaporation residue is taken up in 60 ml of dichloromethane, washed with 60 ml of 0.1 mol/l sodium hydroxide solution; the aqueous phase is counterextracted with 30 ml of dichloromethane, the two organic phases are combined and are dried over a bed of sodium sulfate, followed by filtration and evaporation of the solution to dryness by distillation of the solvent. The residue is taken up in ethanol (55 ml; 12 v) and heated at reflux for 20 minutes (dissolution is not complete) before being cooled to 10° C., the product precipitates and is filtered off with suction on a glass frit; product 4 is washed with two times 9.2 ml of ethanol and then dried under vacuum (3.99 g; yield=89.1%).

HPLC: Basic method; TR=14.9 min
$^1$H NMR (200 MHz, CDCl$_3$): 1.604-2.005 ppm (m, 4H, C$\underline{H}_2$—CH$_2$—CH$_2$—N), 3.677-3.783 ppm (m, 4H, O—C$\underline{H}_2$—CH$_2$—O), 4.019 ppm (t, 2H, CH$_2$—N), 7.500 (t, 1H, Ar), 7.600-8.000 (m, 4H, phthalimide), 8.150 (d, 1H, Ar), 8.300 (s, 1H, Ar)

Molecule 5

Substance 4 (3.987 g; 10.4 mmol) is suspended in methanol (210 ml; 53 v) and then admixed at ambient temperature with hydrazine (15.2 ml; 313 mmol). The reaction is terminated after 20 minutes. The reaction mixture is evaporated to dryness and the residue is taken up in 100 ml of ethyl acetate and washed with 100 ml of water; the aqueous phase obtained is extracted with two times 100 ml of ethyl acetate followed by three times 100 ml of dichloromethane. All the organic phases are combined, evaporated under reduced pressure and placed on a silica gel column (Φ=5 cm, h=15 cm, f=5 cm/min) with the following as eluent: dichloromethane/methanol/aqueous ammonia: 90/10/1.

At the end this gives compound 5 (2.11 g; yield=80.1%).
TLC eluent: dichloromethane/methanol/aqueous ammonia: 90/10/3
HPLC: Basic method; TR=4.8 min
$^1$H NMR (200 MHz, DMSO): 1.464-1.666 ppm (m, 4H, C$\underline{H}_2$—CH$_2$—NH$_2$), 1.904-1.985 ppm (M, 2H, —C$\underline{H}_2$—CH$_2$—C$\underline{H}_2$—NH$_2$); 2.689 ppm (t, 2H, CH$_2$—NH$_2$), 3.753-4.115 ppm (m, 4H, O—CH$_2$—CH$_2$—O), 7.540 ppm (t, 1H, Ar), 7.837 ppm (d, 1H, Ar), 8.147 ppm (d, 1H, Ar), 8.331 ppm (s, 1H, Ar)

Molecule 6

Biotin (6.00 g; 24.5 mmol) is dissolved in anhydrous DMF (60 ml; 10 v) and the solution is then admixed under argon with pyridine (2.44 ml; 30.0 mmol) followed by pentafluorophenyl trifluoroacetate (5.258 ml; 30.5 mmol), and this mixture is heated at 40° C. for 30 minutes and then allowed to return to ambient temperature overnight. After a check—the reaction is terminated—the DMF is evaporated and the residue is taken up in 200 ml of dichloromethane; the product remains in suspension, and is filtered off with suction, the filter cake being rinsed with three times 5 ml of dichloromethane, and the solid product is then dried under vacuum in an oven at 25° C. This gives a product which is very clean in TLC (6.18 g; 61.3%).

TLC eluent: dichloromethane/methanol: 90/10
HPLC: Basic method; TR=10.0 min
$^1$H NMR (200 MHz, DMSO): 1.2-1.8 ppm (m, 6H), 2.3-3.4 ppm (m, 5H), 4.0-4.4 ppm (m, 2H), 6.1-6.6 ppm (m, 2H)

Molecule 7

Reagent 5 (500 mg; 1.98 mmol) is dissolved in a mixture of DMF (5 ml; 10 v) at 60° C. and triethylamine (2.22 ml; 15.8 mmol); in parallel, compound 6 is also dissolved in 4.9 ml of DMF at 60° C. The solution of 6 is run into the solution of 5, and the mixture is stirred at ambient temperature overnight. It is evaporated to dryness without further treatment.

Molecule 8

Substance 7 (948 mg; 1.98 mmol) is reacted with 80% acetic acid (5 ml; 5.3 v) at reflux for 16 hours (NB: it is possible to use 6 M hydrochloric acid, which is much more reactive). The reaction is monitored by HPLC, and must be complete. The acetic acid is evaporated by distillation under vacuum and then the residue is taken up in 500 ml of a dichloromethane/methanol 90/10 mixture and washed with 250 ml of 0.1 M sodium hydroxide solution. The organic phase thus purified is dried over sodium sulfate, filtered and evaporated to dryness. This gives compound 8 (244.8 mg; 28.4%). The product is used in crude form without further treatment.

TLC eluent: not used; impossible to differentiate the starting product form the eventual product
HPLC: Basic method; TR=9.9 min Molecule 9

Compound 8 is taken up in a mixture of DMF (2.49 ml; 12.3 v) and methanol (12.5 ml; 51 v) and admixed with acetic acid (640 μl; 11.1 mmol); the starting product is not soluble. Finally, hydrazine (271 μl; 5.57 mmol) is added, the reagent dissolves, and the solution becomes yellow. After 5 hours of stirring at ambient temperature, all of the solvents are evaporated and are co-evaporated with three times 10 ml of water. The crude reaction product is taken up with 8 ml of milliQ water in a 15 ml tube at 5° C., the product precipitates, the system is stirred for 30 seconds and then the tube is centrifuged at 8500 rpm for 3 minutes; the supernatant is withdrawn and the operation is repeated twice. In the course of the final wash, the pH of the water is verified and is indeed 7; there is no longer any trace of acid.

HPLC: Basic method; TR=8.4 min
$^1$H NMR (200 MHz, DMSO): 1.1-1.9 ppm (m, 8H, —C$\underline{H}_2$—), 2.085 ppm (t, 2H, CO—CH$_2$), 2.50-2.90 ppm (m, 4H, biotin), 3.00-3.20 ppm (m, 3H), 3.30-3.40 ppm (m, 2H), 4.0-4.4 ppm (m, 2H, biotin), 6.30 and 6.50 ppm (2s, 2H, NH biotin), 7.23 ppm (s, 2H, NH), 7.866 ppm (d, 2H, Ar), 8.155 (s, 2H, Ar)

Molecule 10

Powder 9 (250 mg; 0.56 mmol) is taken up in DMF (4.65 ml; 18.6 v), cooled to −5° C., and admixed with tetramethylguanidine (571 μl; 4.53 mmol) followed by 3 Å molecular sieve (957 mg) and manganese oxide (3.03 g; 45.3 mmol). The reaction mixture is stirred at −5° C. under argon for 40 minutes and then filtered on a plug of 1 cm of celite; the plug is then rinsed with methanol until the filtrate becomes colorless. This filtrate is recovered and is evaporated under reduced pressure (bath temperature; 35° C. maximum). The evaporation residue is taken up in 4 ml of dichloromethane/methanol mixture: 90/10 in a 15 ml tube and then washed with 4 ml of 0.1 M sodium hydrogencarbonate solution. The supernatant is removed after centrifugation. The dichloromethane phase is admixed with 350 μl of methanol and 4 ml of sodium hydrogencarbonate, this system is mixed and decanted, the aqueous phase is removed, the final organic phase is dried using anhydrous sodium carbonate, this system is filtered, and the filtrate is evaporated to dryness under reduced pressure. This gives an orange powder (196.8 mg; yield=79.3% over the two last steps).

HPLC: Basic method; TR=11.05 min $^1$H NMR (200 MHz, DMSO): 1.1-1.9 ppm (m, 8H, $CH_2$—), 2.058 ppm (t, 2H, CO—$CH_2$), 2.4-3.4 ppm (m, 7H), 3.0-3.2 ppm (m, 5H), 4.0-4.3 ppm (m, 2H, biotin), 6.33 and 6.40 ppm (2s, 2H, NH biotin), 7.36 ppm (d, 1H, Ar), 7.50-7.70 ppm (m, 2H, Ar+NH), 7.80-7.90 ppm (m, 3H, Ar).

Results and Conclusions:

We have shown that it is possible to synthesize a third generation of molecules. This synthesis is much simpler than those associated with the preceding generations of molecules.

For instance, the second-generation molecules require synthesis in eleven steps, which are relatively complex and laborious.

Moreover, the synthesis pathway for the second-generation molecules is not very versatile. The new synthesis pathway, which is subject matter of the invention, is much more versatile—that is, other aromatic substrates can be used, following the same pathway, in order to increase the diversity of the end-product molecules.

EXAMPLE 2

Synthesis of Para Nitro DKB

Objective:

To demonstrate the feasibility of the synthesis of a DKB molecule, para nitro DKB.

Figure 3:
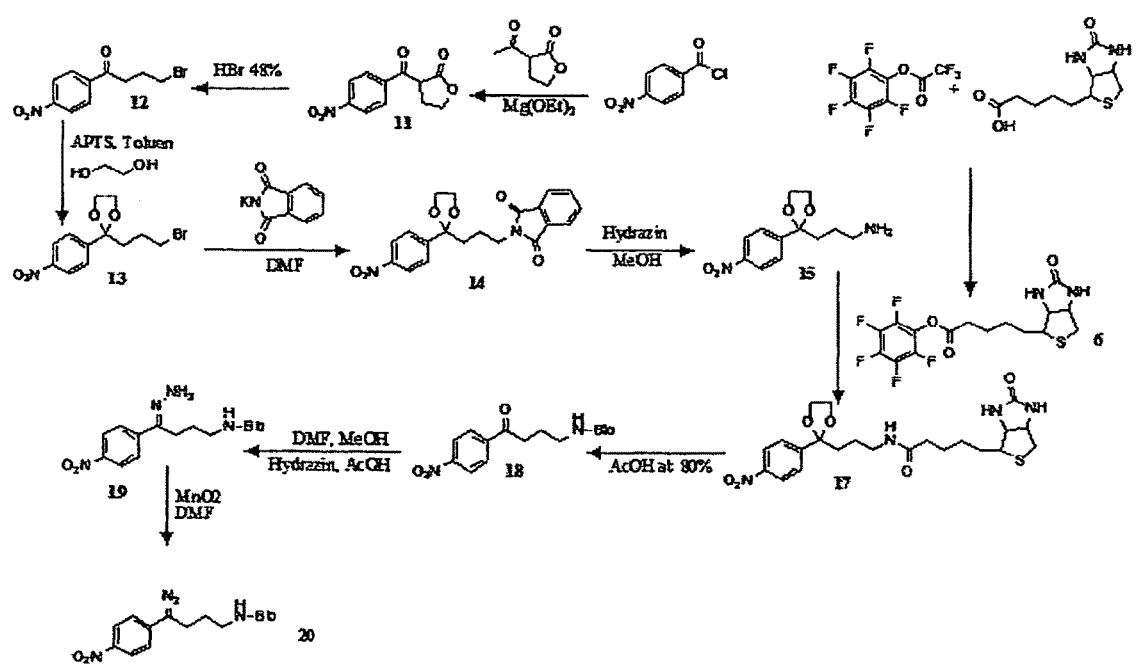
FIG. 3 represents a reaction scheme of the method of synthesizing a para Nitro DKB molecule.

Procedure:

The synthesis proper is shown in FIG. 3. The starting product is para nitro benzyl chloride (Aldrich, St Quentin Fallavier, France). The various molecules synthesized below follow exactly the same procedures as described in example 1.

Molecule 11
  TLC eluent: dichloromethane/methanol: 95/5
  HPLC: Basic method; Tr=1.8 min
  $^1$H NMR (200 MHz, DMSO): 2.40-2.90 ppm (m, 2H, $CH_2$—$CH_2$O), 4.432 ppm (M, 2H, $CH_2$O), 5.153 ppm (t, 1H, C=O—CH—C=O), 8.303 ppm (d, 2H, Ar), 8.382 ppm (d, 2H, Ar)
  MS: [M-H$^+$]$^-$ at m/z=234.3.

Molecule 12
  TLC eluent: dichloromethane/methanol: 95/5
  HPLC: Basic method; TR=13.9 min
  $^1$H NMR (200 MHz, DMSO): 2.189 ppm (qu, 2H, $CH_2$—$CH_2$Br), 3.177 ppm (t, 2H, $CH_2$Br), 3.624 ppm (t, 2H, $CH_2$—CO), 8.217 ppm (d, 2H, Ar), 8.334 (d, 2H, Ar)

Molecule 13
  TLC eluent: cyclohexane/ethyl acetate: 85/15
  HPLC: Basic method; TR=15.5 min
  $^1$H NMR (200 MHz, DMSO): 1.80-2.10 ppm (m, 4H, $CH_2$—$CH_2$—$CH_2$Br), 3.415 ppm (t, 2H, $CH_2$Br), 3.767 ppm (t, 2H, $CH_2$—O), 4.077 ppm (t, 2H, $CH_2$—O), 7.669 ppm (d, 2H, Ar), 8.186 (d, 2H, Ar)

Molecule 14
  HPLC: Basic method; TR=15.1 min
  $^1$H NMR (200 MHz, CDCl$_3$): 1.50-1.65 ppm (m, 4H, $CH_2$—$CH_2$—$CH_2$—N), 3.65-3.70 ppm (m, 4H, $CH_2$—O and $CH_2$—N), 4.00-4.10 ppm (M, 2H, $CH_2$—O), 7.55-7.65 (M, 2H, Ar), 7.65-7.75 (M, 2H, phthalimide), 7.80-7.90 ppm (M, 2H, phthalimide) 8.192 ppm (M, 2H, Ar)

Molecule 15
  TLC eluent: dichloromethane/methanol/aqueous ammonia: 90/10/3
  HPLC: Basic method; TR=5.0 min
  $^1$H NMR (200 MHz, DMSO): 1.30-1.60 ppm (m, 4H, $CH_2$—$CH_2$—$NH_2$), 1.80-2.00 ppm (M, 2H, $CH_2$—$CH_2$—$CH_2$—$NH_2$); 2.678 ppm (t, 2H, $CH_2$—$NH_2$), 3.769 ppm (M, 2H, O—$CH_2$), 4.060 ppm (M, 2H, O—$CH_2$), 7.66 ppm (M, 2H, Ar), 8.177 ppm (M, 2H, Ar)

Molecules 17
  HPLC: Basic method; TR=9.1 min
  TLC eluent: dichloromethane/methanol: 90/10

Molecule 18
  TLC eluent: not used; impossible to distinguish the starting product from the eventual product.
  HPLC: Basic method; TR=9.0 min
  $^1$H NMR (200 MHz, DMSO): 1.2-1.7 ppm (m, 8H, $CH_2$—), 2.093 ppm (t, 2H, CO—$CH_2$), 2.4-3.0 ppm (m, 2H, biotin), 3.0-3.2 ppm (m, 5H), 4.0-4.4 ppm (m, 2H, biotin), 6.34 and 6.40 ppm (2s, 2H, NH biotin), 7.70-7.90 ppm (m, 2H, Ar+NH), 8.20-8.50 ppm (m, 2H, Ar), 8.63 ppm (s, 1H, Ar)

Molecule 19
  HPLC: Basic method; TR=8.2 min

Molecule 20
  HPLC: Basic method; TR=10.7 min
  $^1$H NMR (200 MHz, DMSO): 1.2-1.9 ppm (m, 8H, $CH_2$—), 2.066 ppm (t, 2H, CO—$CH_2$), 2.5-3.0 ppm (m, 4H), 3.0-3.2 ppm (m, 2H), 4.00-4.40 ppm (m, 2H, biotin), 6.36 and 6.42 ppm (2s, 2H, NH biotin), 7.19 ppm (d, 2H, Ar), 7.875 ppm (t, 1H, NH), 8.133 ppm (d, 2H, Ar).

Results and Conclusions:

The steps in synthesizing the para nitro DKB molecule are identical to those described above for the synthesis of the meta nitro DKB molecule; all that is needed is to start with a molecule of para nitro benzyl chloride, or 4-nitrobenzoyl chloride, in place of the molecule of meta nitro benzyl chloride, or 3-nitrobenzoyl chloride.

EXAMPLE 3

Demonstration of the Stability of Meta or Para Nitro DKB Relative to a BBP (Bis-Bio-PDAM) Molecule in Liquid Medium at Ambient Temperature Objective:

To demonstrate the stability in liquid medium of DKB molecules in comparison to a second-generation molecule. For this purpose, an accelerated stability study is carried out under extreme conditions, in which the compounds are stored at 125 mM in a 96/4 DMSO/methanol mixture at ambient temperature (22° C.+/−1° C.). Note that these are extreme storage conditions.

Figure 4:
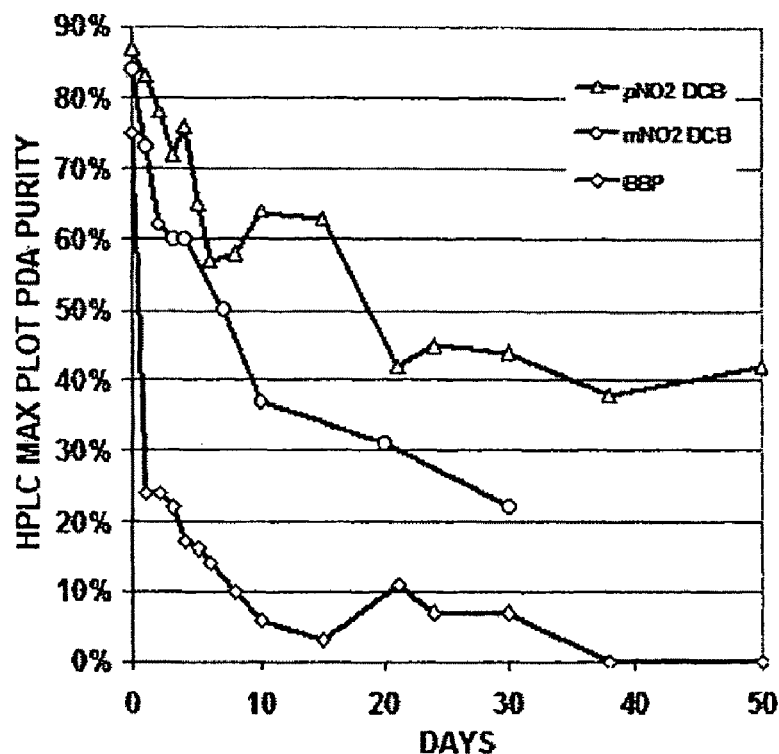
FIG. 4 shows the comparative stability in liquid medium of DKBs relative to a second-generation [Bio-EG3]2-PDAM molecule (referred to hereinafter as BBP), which is described in patent application WO-A-02090319.
Figure 10:
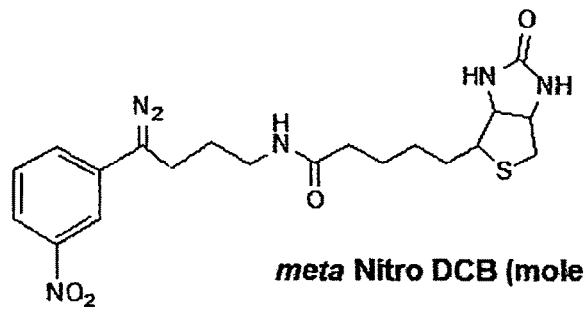
FIG. 10 is a summary of the molecules used in the present patent specification.
Figure 10:
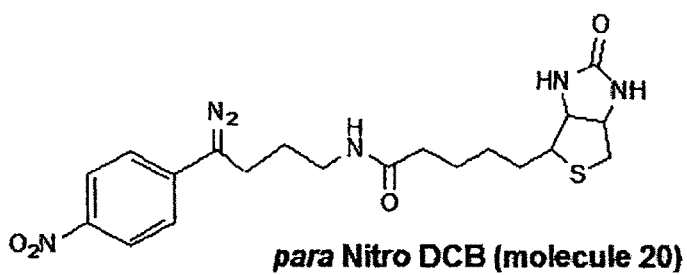
Figure 10:
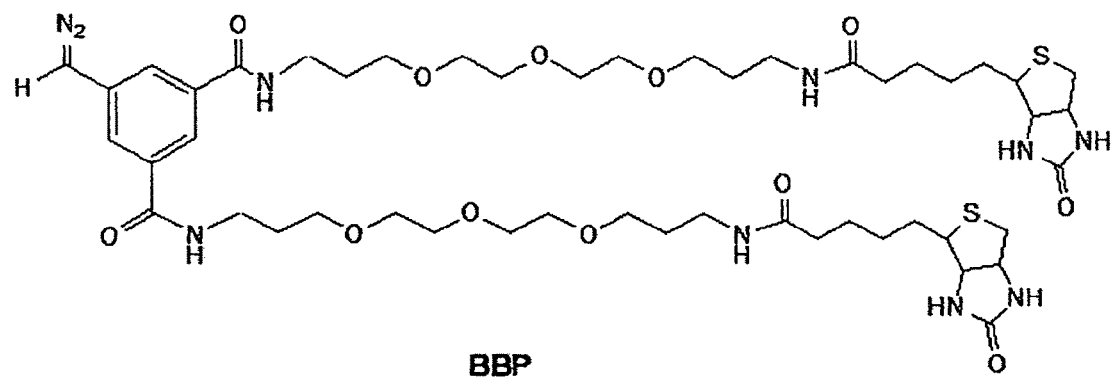

Procedure:

The three compounds meta nitro DKB, para nitro DKB, and BBP, which are clearly shown in FIG. 10, are dissolved at 125 mM in a 96/4 DMSO/methanol mixture and are stored at ambient temperature (22° C. plus or minus 1° C.). At regular intervals subsequently, 2 µl of these solutions are injected in HPLC (basic method, Waters HPLC system) in order to measure the degradation of the principal product by integrating all of the peaks in the chromatogram (PDA Max Plot in the Empower 2 software). The change in the purity of the initial compound as a function of time is then reported, as clearly shown in FIG. 4.

Results and Conclusions:

It is shown unambiguously that BBP breaks down within several days (<10% of purity at 10 days), whereas the DKBs remain much more stable (>40% purity after 2 months of storage for para nitro DKB). The combination of the nitro aryl unit alpha and of the label alpha' of the diazo function stabilizes the diazo function, both by electronic delocalization and by a steric effect, which make the diazo function less susceptible to hydrolysis.

EXAMPLE 4

Demonstration of the Stability of Meta or Para Nitro DKB Relative to a BBP Molecule, in Dry Form at 4° C.

Objective:

To demonstrate the dry stability of DKB molecules in comparison with a second-generation BBP molecule.

Figure 5:
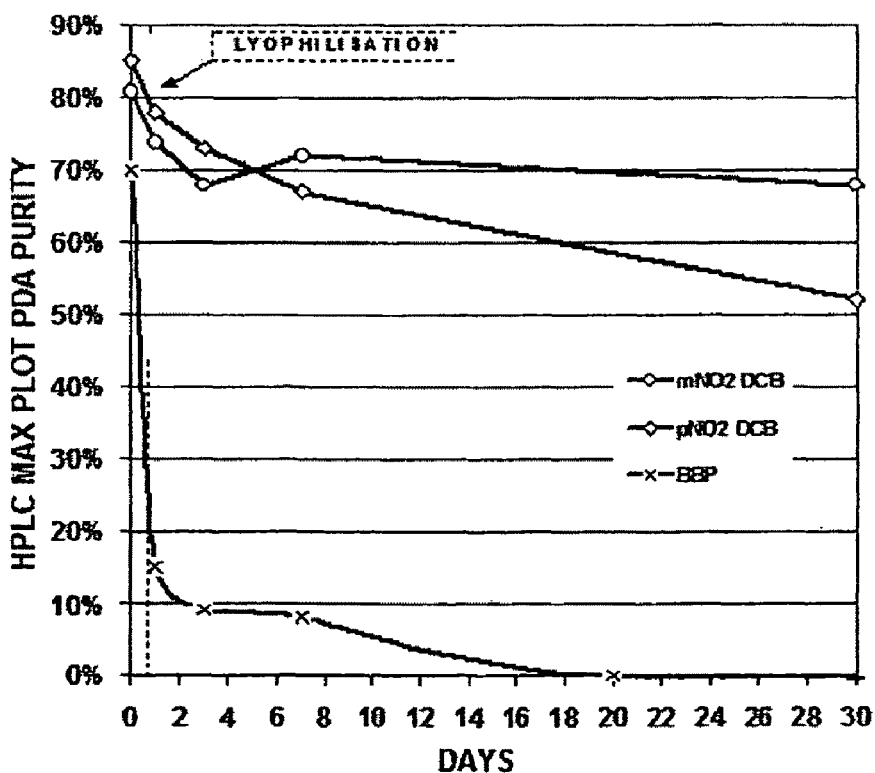
FIG. 5 shows the comparative stability in dry form of DKBs relative to a BBP.

Procedure:

The three compounds meta nitro DKB, para nitro DKB, and BBP are dissolved at 250 mM in a Tris HCl 10 mM, pH 7.5, and 10% Trehalose solution. The solutions are lyophilized overnight in aliquots of 50 nmol. The dry products are then stored at 4° C. At regular intervals these aliquots are dissolved in methanol and 15 µl of these solutions are injected in HPLC (Waters) in order to measure the degradation of the principal product by integration of all of the peaks in the chromatogram (PDA Max Plot in the Empower software). The change in the purity of the initial compound as a function of time is then reported, as clearly shown in FIG. 5.

Results and Conclusions:

In the same way as in example 3, but even more notably, it is demonstrated that BBP does not withstand lyophilization (>60% breakdown during this step), whereas the DKBs remain perfectly stable, particularly so for meta nitro DKB. Once again it is demonstrated that the combination of the nitro aryl unit alpha to the diazo function, and the label alpha', considerably stabilizes said function, making it less susceptible to hydrolysis.

EXAMPLE 5

Labeling of Nucleic Acids with Meta or Para Nitro DKB Relative to a BBP Molecule, with Intermediate Purification Objective:

To demonstrate the effectiveness of the labeling of nucleic acids with DKB molecules in comparison to a second-generation molecule (BBP).

For this purpose, RNA amplicons, fragments of the 174-base sequence of *Mycobacterium tuberculosis*, obtained from an amplification reaction (NASBA, NucliSens Basic Kit from bioMerieux B.V., Boxtel, The Netherlands) are labeled with biotin by reaction with DKBs. The products of the labeling reaction are detected by hybridization on an Affymetrix DNA chip (Custom DNA Chip Combo Myco described in J. Clin. Microbial., 37(1), PP49-55, A. Troesch et al., 1999).

Procedure:

The following components are mixed in a tube:
  18 µl of label solution at 250 mM (DMSO/methanol 96/4), either of DKB or BBP,
  12 µl of DMSO,
  15 µl of NASBA 0.5× buffer ("NucliSens Basic Kit Easy Q, bioMérieux"),
  35 µl of 1 M Tris HCl,
  5 µl of NASBA 0.1× (NASBA amplification reaction, diluted ten times, 174-base amplicon),
  15 µl of 20 mM HCl or 15 µl of water, and
  15 µl of water as a non-HCl control.

The solution is vortexed and then incubated at 65° C. for 10 minutes.

Purification of Nucleic Acids:

The labeled nucleic acids were purified on a QiaQuick column (PCR purification kit QiaQuick, Qiagen, Hilden, Germany), using the purification protocol recommended by the manufacturer. The elution volume is 100 µl.

Hybridization on DNA Chip:

Following purification, the labeled nucleic acids are transferred to 400 µl of hybridization buffer. The samples are hybridized on DNA chips designed for analysis of the "GenBank" M20940 sequence of the 16S RNA of *Mycobacterium tuberculosis*. This DNA chip is described by A. Troesch et al., published in J. Clin. Microbiol., 37(1), PP49-55, 1999.

The hybridization steps are carried out on FS 450 fluidics stations (Affymetrix, Santa Clara, Calif., USA), utilizing the hybridization protocol and the buffers described in the above publication by A. Troesch et al.

The hybridization is revealed by the coupling of streptavidin (SA) labeled with phycoerythrin (PE), which interacts with the biotin of the labels used under the following conditions:

300 µl of pure water; 300 µl of 100 mM Tris buffer, pH 7/1 M NaCl/0.05% Tween 20/0.005% antifoam; 6 µl of BSA (50 mg/ml); 6 µl of SA-PE (300 µg/ml).

Reading of the DNA Chip:

The reading of the fluorescence emitted at the surface of the DNA chip after labeling and hybridization, and the generation of data for signal intensity and percentage homology, are carried out by the reading systems and software supplied by Affymetrix (Scanner Gene Chip Array and GCOS software). The reading system provides signal intensities and background noise intensities expressed in rfu (relative fluorescence units). The percentage homology (% BC equal to % Right in FIG. 6, but also subsequently in FIGS. 7 and 9) is given relative to a reference sequence, which in this case is the sequence of *Mycobacterium tuberculosis*.

Figure 6:
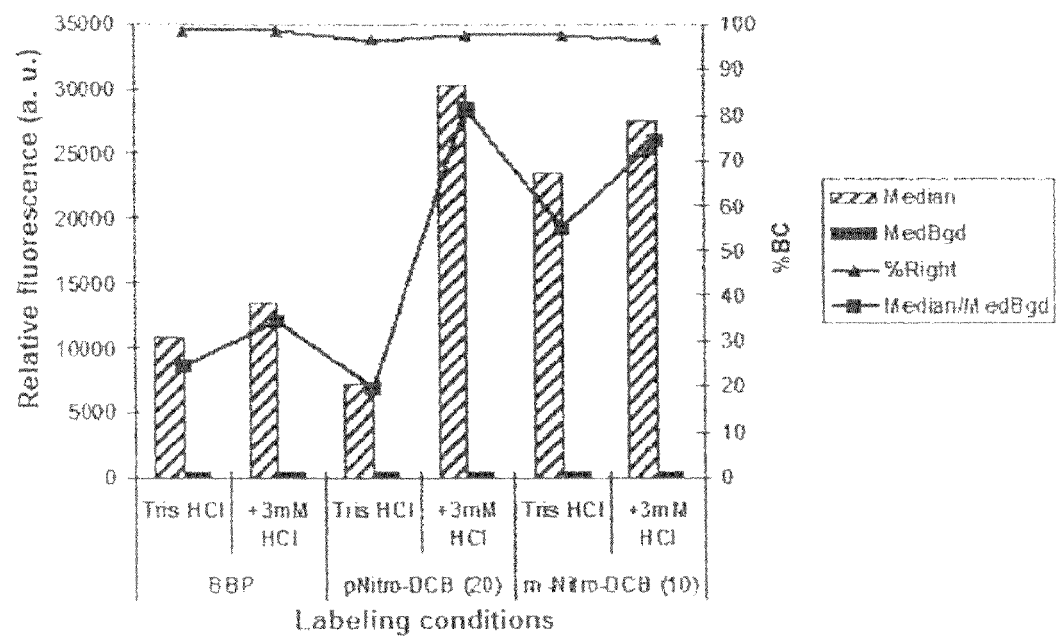
FIG. 6 shows the results of labeling of an RNA amplicon after purification by means of the labels BBP, meta Nitro DKB, and para Nitro DKB, each of the labels being at a concentration of 45 mM.
Figure 7:
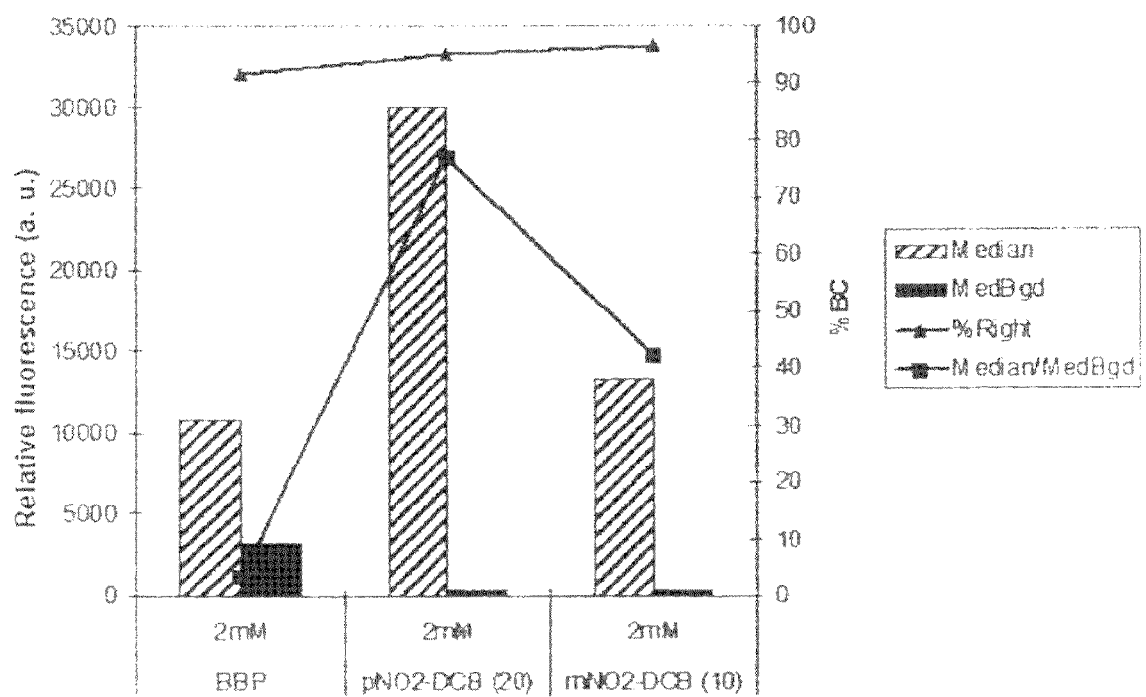
FIG. 7 shows the results of labeling of an RNA amplicon without purification by means of the labels BBP, meta Nitro DKB, and para Nitro DKB, each of the labels being at a concentration of 2 mM and in the presence of 3 mM HCl.

The results in terms of median intensity of the signal (Med), of the background noise (Med Bckgd), and of the percentage homology (% Right) are given in the graph in FIG. 6 for the labels BBP, meta nitro DKB, and para nitro DKB.

Results and Conclusions:

Generally speaking, the main parameter sought is a percentage homology of more than 90%. Secondly, a high specific signal and a low background noise are desired.

This example shows that, in the absence of added hydrochloric acid, the label meta nitro DKB exhibits the best results. In the presence of added 3 mM hydrochloric acid, the labels meta nitro DKB and para nitro DKB, exhibit better results than the BBP reference label.

In all cases, and with account taken of the very high stability of the DKBs, the latter labels show their superiority relative to the molecules of the preceding generations, in that their labeling capacity is at least equal to, if not greater than, that of the second-generation BBP reference molecule.

EXAMPLE 6

Labeling of Nucleic Acids with Meta or Para Nitro DKB Relative to a BBP Molecule, Without Intermediate Purification Objective:

The aim is to demonstrate the same thing as in example 5, but under unfavorable conditions, where the excess of label is not purified.

Procedure:
In a 1 ml tube, the following components are mixed:
5 µl of 8 mM label solution (DMSO/methanol 96/4). The label involved is either DKB or BBP,
5 µl of NASBA 0.1× (NucliSens Basic Kit from bioMérieux),
5 µl of 1 M Tris HCl, and
5 µl of 20 mM HCl.

The solution was vortexed and then incubated at 65° C. for 10 minutes. The nucleic acids labeled in this way are not purified but are hybridized directly.

Hybridization on DNA Chip:
The labeled nucleic acids are transferred without purification to 480 µl of hybridization buffer. The samples are hybridized on the DNA chips in the same way as in the preceding example.

Reading of the DNA Chip:
The results in terms of intensity, background noise, and percentage homology, for the labels BBP, meta nitro DKB, and para nitro DKB, are shown in the graph in FIG. 7.

Results and Conclusions:
This example shows that the labels meta nitro DKB and para nitro DKB have structures which mean that they exhibit reduced background noise relative to the BBP reference molecule. The specific signals are also improved (especially for para nitro DKB), and the percentage homology, which is relatively low for BBP, becomes extremely high for meta nitro DKB.

Once again, the superiority of the third-generation molecules relative to those of the preceding generations is demonstrated.

EXAMPLE 7

Evaluation of the Stability Over 24 Hours of an Amplicon Labeled with Meta or Para Nitro DKB Objective:
The aim is to demonstrate that a labeled RNA amplicon can be hybridized for up to 24 hours on a DNA chip without losing its fluorescence intensity. This demonstrates the stability of the RNA-labeled bond.

Procedure:
The following components are mixed in a tube:
5 µl of label solution (meta nitro DKB or para nitro DKB) at 10 mM in DMSO/MeOH (96/4),
5 µl of NASBA 0.1× amplification product (NucliSens Basic Kit from bioMérieux),
5 µl of 1 M Tris HCl, and
5 µl of water.

The solution is vortexed and then incubated at 65° C. for 10 minutes.

Purification of Nucleic Acids:
The labeled nucleic acids were purified on a QiaQuick column (PCR purification kit, Qiagen), using the purification protocol recommended by the manufacturer. The elution volume is 100 µl.

Hybridization on DNA Chip:
Following purification, the labeled nucleic acids are transferred to 400 µl of hybridization buffer. The samples are hybridized on DNA chips designed for analysis of the "GenBank" M20940 sequence of the 16S RNA of *Mycobacterium tuberculosis*. This DNA chip is described by A. Troesch et al., published in J. Clin. Microbiol., 37(1), pp 49-55, 1999.

The hybridization steps were carried out by injecting 80 µl of the hybridization mixture into the chip and then keeping the chip in a hybridization oven at 45° C. for 0.5 hour, 2 hours, 6.5 hours or 24 hours.

The hybridization is revealed by the coupling of streptavidin (SA) labeled with phycoerythrin (PE), which interacts with the biotin of the labels used under the following conditions:
300 µl of pure water; 300 µl of 100 mM Tris buffer, pH 7/1 M NaCl/0.05% Tween 20/0.005% antifoam; 6 µl of BSA (50 mg/ml); 6 µl of SA-PE (300 µg/ml).

Reading of the DNA Chip:
The reading of the fluorescence emitted at the surface of the DNA chip after labeling and hybridization, and the generation of data for signal intensity and percentage homology, are carried out by the reading systems and software supplied by Affymetrix. The reading system provides signal intensities and background noise intensities expressed in rfu (relative fluorescence units). The percentage homology is given relative to a reference sequence, which in this case is the sequence of *Mycobacterium tuberculosis*.

Figure 8:
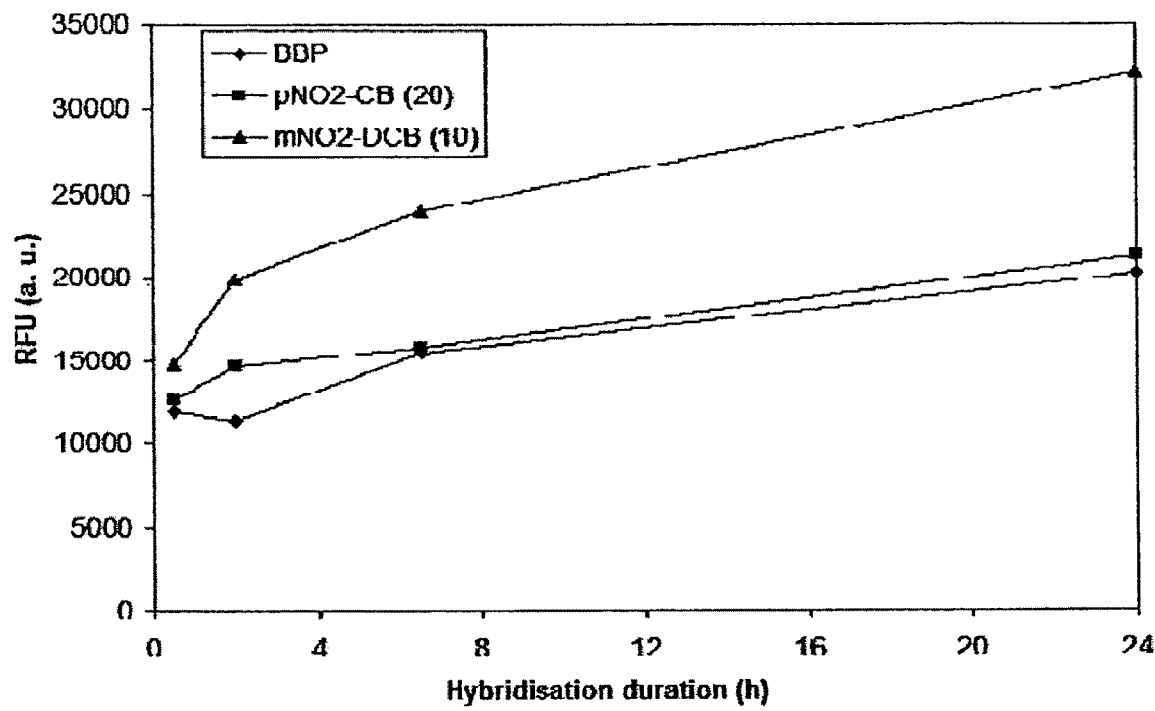
FIG. 8 shows the results of labeling as a function of time of an RNA amplicon by means of the labels meta Nitro DKB and para Nitro DKB, each of the labels being at a concentration of 3 mM and in the presence of 3 mM HCl.

The results in terms of median intensity of the signal (Med), as a function of the hybridization time, are given in FIG. 8 for the labels meta nitro DKB (also called m-NO$_2$-DKB) and para nitro DKB (also called p-NO$_2$-DKB).

They show that the fluorescence signal remains stable and even tends to rise as a function of the hybridization time.

Results and Conclusions:
This example shows that the amplicons labeled with meta nitro DKB or para nitro DKB remain perfectly stable in the course of hybridization, which may be prolonged for 24 hours (of particular advantage for long hybridizations and gene expression in oncology); see FIG. 8.

There is even an increase observed in the fluorescence signal over time, which is due to better hybridization of the amplicons (the hybridization kinetics are slow).

This therefore demonstrates the stability of the label-nucleic acid bond.

EXAMPLE 8

Comparison of the Efficiency of Labeling of Molecules Described in the Present Invention with that of a Commercially Available Technology (ULS RNA Labelling Kit, Kreatech, the Netherlands)

Procedure:
The RNA amplicons are prepared by a NASBA amplification as before, and are labeled with the BBP, p-NO$_2$-DKB or m-NO$_2$-DKB molecules.

The following components are mixed in a tube:
5 µl of NASBA 1× (NucliSens Basic Kit from bioMérieux),
5 µl of label solution at 20 mM (BBP, p-NO$_2$-DKB or m-NO$_2$-DKB in DMSO/methanol 96/4,
5 µl of 1 M Tris HCl, pH 7.4, and
5 µl of water.

The solution was vortexed and then incubated at 65° C. for 10 minutes.

For labeling with the commercial kit from Kreatech, the protocol recommended by the manufacturer was followed. In summary, the following are mixed:
20 µl of NASBA 1× (NucliSens Basic Kit from bioMérieux),
1 µl of label solution,
3 µl of 10× buffer, and
6 µl of water.

The solution was incubated at 85° C. for 30 minutes.

Purification of Nucleic Acids:

The nucleic acids labeled using the BBP, p-NO$_2$-DKB or m-NO$_2$-DKB molecules were purified on a QiaQuick column (PCR purification kit, Qiagen), using the purification protocol recommended by the manufacturer. The elution volume is 100 µl.

For the nucleic acids labeled using the commercial kit, the purification recommended and supplied by Kreatech was used. The final volume is 30 µl, to which are added 100 µl of a blocking solution recommended by that company.

Hybridization on DNA Chip:

Following purification, the labeled nucleic acids are transferred to 400 µl of hybridization buffer (BBP, p-NO$_2$-DKB or m-NO$_2$-DKB) or 370 µl of hybridization buffer (Kreatech). Said nucleic acids are hybridized on DNA chips designed for analysis of the "GenBank" M20940 sequence of the 16S RNA of *Mycobacterium tuberculosis*.

This DNA chip is described by A. Troesch et al., published in J. Clin. Microbiol., 37(1), PP49-55, 1999. The hybridization steps were carried out on fluidics stations (Affymetrix FS 450), utilizing the hybridization protocol and the buffers described in said publication by A. Troesch et al.

The hybridization is revealed by the coupling of streptavidin (SA) labeled with phycoerythrin (PE), which interacts with the biotin of the labels used under the following conditions:

300 µl of pure water; 300 µl of 100 mM Tris buffer, pH 7/1 M NaCl/0.05% Tween 20/0.005% antifoam; 6 µl of BSA (50 mg/ml); 6 µl of SA-PE (300 µg/ml).

Reading of the DNA Chip:

The reading of the fluorescence emitted at the surface of the DNA chip after labeling and hybridization, and the generation of data for signal intensity and percentage homology, are carried out by the reading systems and software supplied by Affymetrix (Gene Chip Array and GCOS software). The reading system provides signal intensities and background noise intensities expressed in rfu (relative fluorescence units). The percentage homology is given relative to a reference sequence, which in this case is the sequence of *Mycobacterium tuberculosis*.

Figure 9:
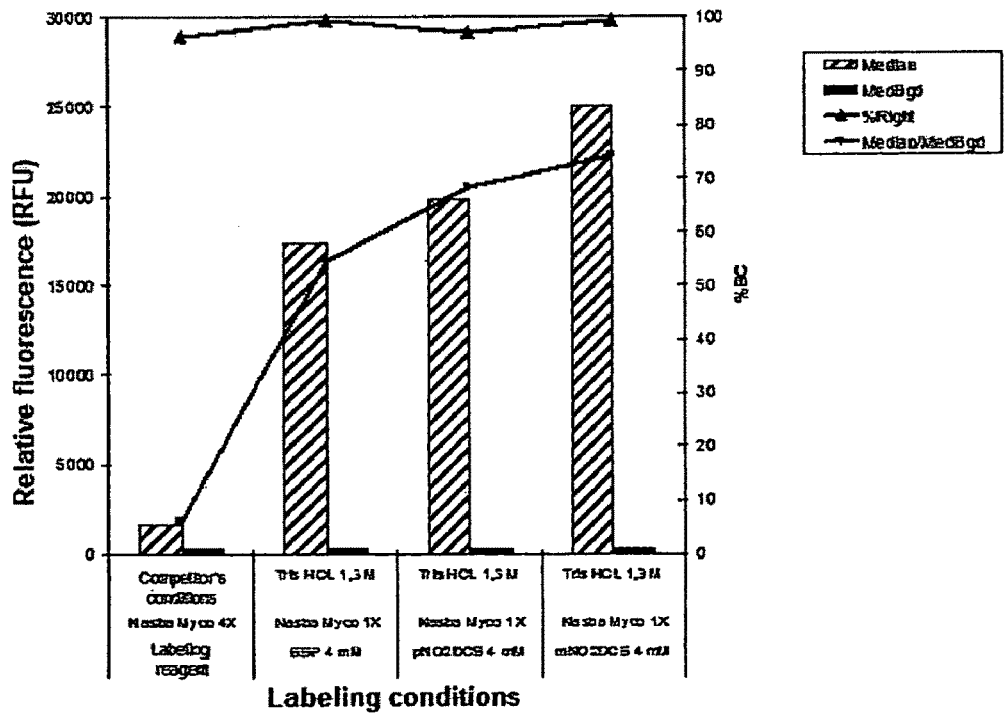
FIG. 9 shows a comparison of the effectiveness of labeling an RNA amplicon as a function of the technique employed: either ULS (Universal Labelling System) from Kreatech, or in accordance with the present invention.

The results in terms of median intensity of the signal (Med), of the background noise (Med Bckgd), and of the percentage homology (% BC) are given in FIG. 9 for the labels BBP, m-NO$_2$-DKB, and p-NO$_2$-DKB and also for the competitor kit.

Results and Conclusions:

It is found that the technology using the cis-platin labels from Kreatech (which is applied in exactly the conditions described by the supplier) has a much lower labeling potential than the technical solution provided by the present invention, since in the case of Kreatech it is necessary to add more than four times the concentration of RNA in order to obtain a signal which is clearly separate from the background noise (FIG. 9), but which in all cases remains more than ten times weaker than the labeling produced with the DKB or BBP molecules.

In all cases, the percentage identity (% BC) remains the same.

Labeling on the internucleoside linkages, in comparison to another labeling technique, therefore makes it possible to obtain a much better sensitivity of detection, irrespective of the generations of molecules.

The invention claimed is:

1. A labeling reagent of formula (A):

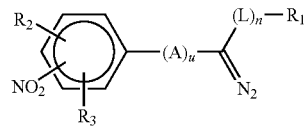

in which:

R$_1$ represents a detectable label or at least two detectable labels linked to one another by at least one multimeric structure, R$_2$ and R$_3$ represent, independently of one another: H, NO$_2$, Cl, Br, F, I, R$_4$, OR, SR, NR$^2$, R, NHCOR, CONHR or COOR, with R being alkyl or aryl, and R$_4$ represents a detectable label or at least two detectable labels linked to one another by at least one multimeric structure, L is a linker arm comprising a linear chain of at least two covalent bonds, n is an integer from 1 to 20, A is a linker arm comprising at least one covalent double bond allowing the conjugation of the diazo function with the aromatic ring, and u is an integer between 0 and 2.

2. A labeling reagent as claimed in claim 1, of formula (C):

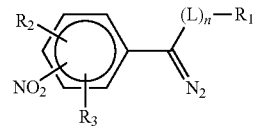

in which:

R$_1$ represents a detectable label or at least two detectable labels linked to one another by at least one multimeric structure, R$_2$ and R$_3$ represent, independently of one another: H, NO$_2$, Cl, Br, F, I, R$_4$, OR, SR, NR$^2$, R, NHCOR, CONHR or COOR, with R being alkyl or aryl, and R$_4$ represents a detectable label or at least two detectable labels linked to one another by at least one multimeric structure, L is a linker arm comprising a linear chain of at least two covalent bonds, and n is an integer equal to 1.

3. A labeling reagent as claimed in claim 1, of formula (E):

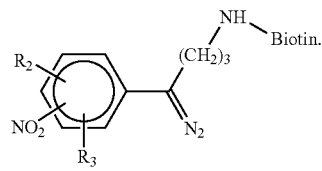

4. A reagent as claimed in claim 1, wherein the nitro group is in meta or para position.

5. A reagent as claimed in claim 1, wherein R$_1$ is composed of a D-biotin residue of formula (F):

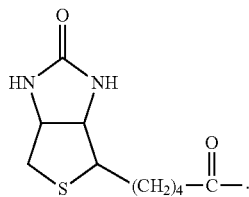

6. A method of synthesizing a labeling reagent as claimed in claim 1, comprising the following steps:
 a) a carboxylic acid derivative is reacted with the enolate of a lactone (Claisen reaction) to form a cyclic precursor,
 b) said cyclic precursor is subsequently opened with a halogen acid to form a halogenated aromatic ketone,
 c) the carbonyl function of the halogenated aromatic ketone is protected by a protective group to form a protected precursor,
 d) said protected precursor is subjected to an amination reaction (Gabriel reaction) to form an aminated precursor,
 e) said aminated precursor is deprotected to liberate the amine function, said amine function being reacted with a detectable label whose carboxyl function is activated to form a precursor comprising a detectable label,
 f) the labeled precursor is subjected to a reaction for deprotection of the carbonyl function, to form a labeled and carbonylated precursor, and lastly
 g) the labeled and carbonylated precursor is converted into the labeling reagent of claim 1 by conversion of the carbonyl function into a diazo function (Bamford Stevens reaction).

7. A method of labeling a biological molecule, comprising contacting a biological molecule, in homogeneous solution in a substantially aqueous buffer, with a reagent as claimed in claim 1.

8. A labeled biological molecule obtainable by the method as claimed in claim 7.

9. A method of labeling and fragmenting a single-stranded or double-stranded nucleic acid, comprising the following steps:
 fragmenting the nucleic acid;
 attaching a label to at least one of the fragments via a labeling reagent selected from the reagents as claimed in claim 1,
 said reagent coupling covalently and predominantly to at least one phosphate of said fragment.

10. The method as claimed in claim 9, wherein fragmenting and labeling are performed in two steps.

11. The method as claimed in claim 9, wherein fragmenting and labeling are performed in one step.

12. The method as claimed in claim 9, wherein labeling is performed in substantially aqueous homogeneous solution.

13. The method as claimed in claim 9, wherein fragmenting is performed enzymatically, physically or chemically.

14. A labeled nucleic acid obtainable by the method as claimed in claim 9.

15. A kit for detecting a target nucleic acid, comprising a labeled nucleic acid as claimed in claim 14.

16. A solid support on which is bound a reagent as claimed in claim 1.

17. A method of capturing nucleic acids, comprising the following steps:
 providing a solid support on which is bound, directly or indirectly, at least one biological molecule as claimed in claim 8, the biological molecule comprising a diazomethyl function,
 contacting said support with a biological sample which may contain free nucleic acids, and
 washing the solid support where the molecule or molecules is/are bound covalently at least to a nucleic acid.

18. The reagent of claim 1, wherein L is a linear chain linker arm comprising at least two covalent bonds.

19. The reagent of claim 18, wherein L is (O—$CH_2$—$CH_2$), and n is from 1 to 20.

20. The reagent of claim 18, wherein L is ($CH_2$), and n is from 1 to 3.

* * * * *